United States Patent [19]

Jacobs

[11] Patent Number: 4,804,685

[45] Date of Patent: Feb. 14, 1989

[54] BUFFERED GLUTARALDEHYDE STERILIZING AND DISINFECTING COMPOSITIONS

[75] Inventor: Paul T. Jacobs, Arlington, Tex.

[73] Assignee: Surgikos, Inc., Arlington, Tex.

[21] Appl. No.: 660,198

[22] Filed: Oct. 12, 1984

[51] Int. Cl.$^4$ ............................................. A01N 35/00
[52] U.S. Cl. ................................... 514/698; 514/705; 514/970
[58] Field of Search ............................. 424/333, 211; 252/DIG. 11; 514/698, 705, 970

[56] References Cited

U.S. PATENT DOCUMENTS

| | | | |
|---|---|---|---|
| 3,016,328 | 1/1962 | Pepper et al. | 424/127 |
| 3,282,775 | 11/1966 | Stonehill | 424/263 |
| 3,868,217 | 2/1975 | Hollingshad | 21/2.7 A |
| 3,925,228 | 12/1975 | Cheng | 252/DIG. 11 |
| 3,983,252 | 9/1976 | Buchalter | 424/333 |
| 4,048,336 | 9/1977 | Winicov et al. | 424/333 |
| 4,093,744 | 6/1978 | Winicov et al. | 424/333 |
| 4,436,754 | 3/1984 | Jacobs | 424/333 |

Primary Examiner—Allen J. Robinson
Attorney, Agent, or Firm—Michael Q. Tatlow

[57] ABSTRACT

A glutaraldehyde sterilizing and disinfecting solution which is hard water compatible and which contains a nitrilo tris (ethyl phosphoric acid) salt as a buffering agent.

5 Claims, No Drawings

BUFFERED GLUTARALDEHYDE STERILIZING AND DISINFECTING COMPOSITIONS

BACKGROUND OF THE INVENTION

1. Field of the Invention

The present invention relates to sterilizing and disinfecting solutions containing glutaraldehyde as the active ingredient. The present solutions contain an improved buffering composition. The solutions of the present invention are capable of being diluted with hard water without becoming turbid and without any reduction in the efficacy of the solution as a sterilizing or disinfecting solution.

2. Prior Art

Glutaraldehyde solutions are well known as sterilizing and disinfecting agents. These solutions are buffered to maintain the solution at a specific pH range during use. The following United States patents disclose such solutions and various compositions used as the buffering agent.

1. Pepper et al. U.S. Pat. No. 3,016,328, which teaches disinfecting with a sporicidal composition containing saturated dialdehyde, such as glutaraldehyde, and an alkalinating or buffering agent in either an alcoholic solution, or an aqueous solution at above pH 7.4. The alkalinating or buffering agent is an alkali metal carbonate or bicarbonate.

2. Stonehill U.S. Pat. No. 3,282,775, which teaches disinfecting with sporicidal solutions containing a saturated dialdehyde, preferably glutaraldehyde, and a cationic surface active agent. The solutions are buffered with alkali metal carbonates, bicarbonates, phosphates, borates or certain amines such as diethylaminoethanol and dibutylamine.

3. Winicov et al. U.S. Pat. Nos. 4,048,336 and 4,093,744, which teach sporicidal solutions containing glutaraldehyde at pH 6.5 to pH 7.4, which may contain a detergent and also a monoaldehyde. The activator or buffer may be phosphates, citrates, carbonates or bicarbonates.

4. Buchalter U.S. Pat. No. 3,983,252, which teaches disinfectant solutions that contain a dialdehyde in an aqueous solution buffered with an alkali metal salt of a hydrocarbon carboxylic acid in aqueous solution. The solution also contains an alcohol, diol or triol. The compositions are stated to have improved stability in the pH range of from 6.0 to 7.4.

Generally, aqueous glutaraldehyde solutions are stable almost indefinitely within a pH range of 2.5 to 4.5. However, at an acidic pH, glutaraldehyde solutions exhibit poor sporicidal activity. Just prior to use, pH levels of the glutaraldehyde solutions are adjusted through the addition of an alkalinating or activating agent which is the buffering composition for the solution. The addition of the activating agent increases the pH level to above 7 where these compositions have greater sporicidal activity. The normal buffering agents employed are generally inorganic salts such as phosphates, citrates, carbonates or bicarbonates. The commercial solutions are usually packaged with the aqueous glutaraldehyde solution at a pH in the acid range and the activator packaged in a separate container and added to the solution immediately prior to use. When used as a sterilizing composition, the concentration of the glutaraldehyde is normally in the range of 2% to 4% by weight with the remainder of the solution being generally deionized water. When used as an environmental surface disinfectant, the concentration of the glutaraldehyde in the solution may be as low as 0.05%. It has not heretofore been found practical to ship concentrated glutaraldehyde solutions, i.e., 10% to 25% glutaraldehyde, to be diluted at the point of use with tap water because of the variation in the quality of the tap water. The hardness of the tap water causes problems with the buffering or activator compositions for the solutions. In very hard water, the normal phosphate type activators will react with calcium and magnesium salts in the tap water to form an insoluble precipitate. This insoluble precipitate causes the active solutions to become turbid and the precipitate may deposit on the surgical instruments which are sterilized by the compositions.

Although it is known that borate salts will not form precipitates with the calcium and magnesium ions found in hard water, the borates have not been found acceptable as the activating composition in glutaraldehyde sterilizing and disinfecting solutions because they have an adverse effect on the biological activity of the solutions in use. That is, a glutaraldehyde solution with a borate activating composition is not as effective in terms of its sporicidal activity as a glutaraldehyde solution activated with a phosphate activator composition. It is also known that chelating agents, such as ethylenediaminetetraacetic acid, will prevent precipitate formation with hard water. However, aqueous glutaraldehyde solutions containing these compounds are corrosive to certain metals used in medical instruments and equipment.

In addition to the problems of intentional dilution with tap water mentioned above, glutaraldehyde solutions are often unintentionally diluted with tap water during use. The unintentional dilution results from the contamination of the solution with rinse water during the normal use of the solution. If the water used for the rinse water has any significant hardness, i.e., 50 ppm or higher, inorganic phosphate buffers in the solution can combine with the calcium and magnesium ions in the water and form an insoluble salt which will precipitate on the devices being sterilized. The reduction in the phosphate ion concentration in the solution may also reduce the sporicidal activity of the solution.

THE PRESENT INVENTION

The present composition contains an activator system which will not precipitate salts when diluted with hard water and also will maintain the sporicidal activity of the glutaraldehyde solution. It is, thus, possible to formulate solutions with an increased concentration of the glutaraldehyde active agent and then dilute these solutions at the point of use with hard water without causing the problems mentioned above. The ideal activator system should be compatible with hard water up to about 500 parts per million (ppm); be an effective buffer in a pH range of from 7 to 9, which is the optimum pH range for sporicidal activity for glutaraldehyde solutions; produce a glutaraldehyde solution which is noncorrosive to the metals used in medical equipment; impart good sporicidal activity to the activated solution; and, provide activative glutaraldehyde solutions with good use life stability.

It has been found that the use of nitrilo tris (ethylphosphoric acid) salts, particularly the sodium and potassium salt, meets the above requirements. The formulation of this compound is:

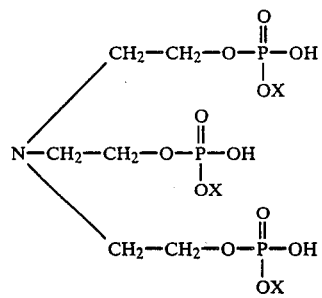

where X is sodium, potassium or hydrogen. The compound is available under the tradename "WAYHIB S" from the Philip A. Hunt Chemical Company. It is available as the sodium salt and can be treated with potassium hydroxide to form a potassium salt or mixed potassium and sodium salt.

The present invention, therefore, provides a solution containing glutaraldehyde which can be used as a sporicidal or sterilizing and a disinfecting solution and which may be formulated at concentrations higher than the normal use concentration and which can be diluted to the use concentration with hard water without effecting the properties of the resulting solution.

As it has been determined that inorganic phosphate salts are excellent buffering compounds when using pure water but form insoluble precipitates when mixed with hard water, organophosphorus compounds were evaluated as the activating or buffering ingredient in various glutaraldehyde solutions. The organophosphorous compounds were tested to determine their buffering capacity and hard water compatability. The compatibility of resulting glutaraldehyde solutions containing the organophosphorous compounds with various metals that are commonly used in surgical instruments was also determined. These metals include carbon steel, stainless steel, brass and nickel. If the solutions corroded these metals, the compound was not considered to be compatible. The organophosphorous compounds were tested for buffering capacity which would indicate their ability to buffer the glutaraldehyde solution in the range of pH 7 to pH 9. The buffering capacity of the materials was determined by titrating 50 grams of a 1.0% active concentration of the test material from pH 9 to pH 7 with 0.2% glutaric acid. The volume in milliliters of glutaric acid required to titrate from pH 9 to pH 7 was defined as the buffering capacity of the solution for that pH range. In order to have utility as an activator for a glutaraldehyde solution, the materials need a minimum buffering capacity of 25. The hard water compatibility was determined using hard water prepared by the Official Methods of the Association of Official Analytical Chemists, 13th Edition, 1980 Section 4.027. The solutions of activator were prepared at equal molar concentrations (0.028 moles) of the activator salt and at a pH of from 7.6 to 8.0. The samples were aged for one hour and the turbidity tested. The turbidity of samples was measured at 640 nm using a Beckman 35 UV-visible Spectrophotometer. Incompatibility of the activator was determined by visible turbidity of the test solution and an absorbance reading in excess of 0.010.

The results of the various tests are shown in Table I.

TABLE I

| | Hard Water Compatibility | Buffering Capacity MLS Glutaric Acid | Metal Compatibility |
|---|---|---|---|
| Ethylenediaminetetra (Methylene Phosphonic Acid) Potassium Salt | Yes | 37.7 | No |
| Hexamethylenediaminetetra (Methylene Phosphonic Acid) | Yes | 14.4 | No |
| Nitrilo tris (Methylene Phosphonic Acid) | Yes | 42.2 | No |
| Diethylenetriaminepenta (Methylenephosphonic Acid) | Yes | 47.5 | No |
| Hydroxyethane -1, 1- Diphosphonic Acid | Yes | 38.5 | No |
| 1-Aminoethane 1, 1,- Diphosphonic Acid | Yes | 50.1 | No |
| Nitrilo tris (Ethyl Phosphoric Acid) Sodium Salt | Yes | 37.5 | Yes |
| Mono (Ethylene Glycol) Phosphoric Acid | No | 38.9 | Yes |
| Mono (Diethylene Glycol) Phosphoric Acid | No | 27.5 | Yes |
| Mono (Tetraethylene Glycol) Phosphoric Acid | Yes | 19.9 | Yes |
| Mono (Hexaethylene Glycol) Phosphoric Acid | No | 14.0 | Yes |
| Mono (Octaethylene Glycol) Phosphoric Acid | No | 10.9 | Yes |

Based on these tests, nitrilo tris (ethyl phosphoric acid) salts were the only materials which meet all the requirements necessary for the use as a buffer in a glutaraldehyde solution.

The solutions of the present invention will contain glutaraldehyde, nitrilo tris (ethyl phosphoric acid) salts and water. The ratio of glutaraldehyde to the nitrilo tris (ethyl phosphoric acid) salt may vary over a wide range. The ratio may vary from 15 to 1 to 1 to 1. The preferred ratio is between 5 to 1 and 2 to 1. The solutions may also contain corrosion inhibitors, surfactants, stabilizers, additional buffering agents fragrances and dyes. The corrosion inhibitors are used to assist in preventing corrosion of surgical instruments. Typical corrosion inhibitors used may be sodium nitrite, tolytriazole or benzotriazole. The surfactant employed may be a nonionic, cationic, anionic or amphoteric and functions as a wetting agent in the solution. Fragrances such as peppermint oil, mint, oil of wintergreen and pine oil may be used to mask the odor of the solution. Dyes or colorant may also be used. The dyes may be pH indicators or may be used in the activator portion of the two-component package to indicate that the activator has been added to the glutaraldehyde solution. All of the above-mentioned additives are used in small amounts in the solution at use concentrations. The amounts of the additives present being from about 0.001 to 1% by weight of the solution.

The composition may also contain a diol as disclosed in U.S. Pat. No. 4,436,754. The diol or monosubstituted diol taught in U.S. Pat. No. 4,436,754 has the formula $RO(CH_2CH_2O)_nCH_2CH_2OH$ wherein R is H or $CH_3$ and n is an integer of from 1 to 22. The presence of the diol in the solution reduces the odor and irritation potential of the glutaraldehyde in the solution. The preferred diol in the present invention is polyethylene glycol with a molecular weight of 194, wherein R=H and n=3. In a solution using the nitrilo tris (ethyl phosphoric acid) salt of the present invention, the preferred weight ratio of diol to glutaraldehyde is from 2 to 1 to 5 to 1.

Typical formulations at use concentrations would contain:

|  | Weight Percent |
| --- | --- |
| Glutaraldehyde | 0.05–3.6 |
| Potassium Acetate | 0.007–1.85 |
| Nitrilo tris (ethyl phosphoric acid) salt | 0.004–1.25 |
| Corrosion Inhibitor | from 0.4 ppm to 0.013% |
| Dye | ppm |
| Water | Q.S. |

The concentration of glutaraldehyde in the formulation at use concentration depends on the intended use of the composition. (The concentration of the ingredients discussed herein will be given in weight percent unless otherwise indicated.) If the composition is intended for use as an environmental surface disinfectant, the glutaraldehyde concentration may be as low as 0.05%. If the composition is intended for use as a sterilizing solution, the glutaraldehyde concentration should be at least 2%. If the composition is intended for use in automatic disinfecting equipment, where it is very likely that the solution will be substantially diluted with rinse water, it is advantageous to use higher concentrations of glutaraldehyde, i.e., 3.6%.

As previously indicated, glutaraldehyde sterilizing and disinfecting solutions are usually distributed with the aqueous glutaraldehyde solution at an acid pH and the activator in a separate container. The glutaraldehyde may be present in the concentrated solution in one container in an amount of from 2.0% to 30% by weight of the concentrated solution. The activator or buffer and other ingredients in a second container are adjusted to give the proper ratio for the amount of glutaraldehyde in the solution in the first container. The glutaraldehyde solution would be activated by mixing the contents of the two containers. If the activated solution is subsequently diluted, the ingredients will be in the proper ratio for effective sterilization or disinfection. The concentration of the ingredients in a concentrated solutions will depend on the desired concentration at use. For example, one part of a 6% concentrated glutaraldehyde solution can be diluted with 11 parts of water to yield a disinfectant having a use concentration of 0.5%. The remaining ingredients in the composition are adjusted to give the desired concentration at use.

EXAMPLE I

A series of glutaraldehyde solutions at different concentrations were prepared to compare the effectiveness of nitrilo tris (ethyl phosphoric acid) salts with dipotassium hydrogen phosphate, which is a well-known activator for glutaraldehyde. Each of the formulations contained the indicated amount of glutaraldehyde and 0.15% of a surfactant composition, 0.80% potassium acetate and 0.023% of $NaNO_2$ as a corrosion inhibitor. The formulations contained either 0.3% of the dipotassium hydrogen phosphate or 0.3% to 0.35% of the nitrilo tris (ethyl phosphoric acid) salt (Activator A in Table II). The formulations were tested against *Bacillus subtilis* spores on silk sutures according to the standard sporicidal test as specified in *Official Methods of Analysis* of the Association of Official Analytical Chemists (AOAC), 13th Edition 1980, Sections 4.015–4.017. The results are shown in Table II. The effectiveness of the glutaraldehyde solutions were also tested against *Clostridium sporogenes* spores on porcelain penicylinders in a modified AOAC procedure. The modification being that the spores were grown in 5% polypeptone-peptone media instead of the standard egg-meat media called for in the test. The results of this test are also shown in Table II.

TABLE II

| Activator | % Glut* | *Bacillus subtilis* Silk Sutures # Failures/ # Tested | *Clostridium sporogenes* Penicylinders # Failures/# Tested |
| --- | --- | --- | --- |
| $K_2HPO_4$ | 1.00 | 5/150 | 0/150 |
| A | 1.00 | 7/150 | 0/150 |
| $K_2HPO_4$ | 1.26 | 7/100 | 0/100 |
| A | 1.30 | 5/100 | 1/100 |

*Glutaraldehyde

The results of tests show that glutaraldehyde solutions containing nitrilo tris (ethyl phosphoric acid) salts are equivalent in sporicidal activity to the solutions containing dipotassium hydrogen phosphate.

EXAMPLE II

Various compositions of glutaraldehyde solutions made with various activators were tested in hard water again using the *Bacillus subtilis* spores on silk sutures at 20° C. with a 10-hour contact time. Tables III and IV show the formulations used in the test, and Tables V and VI show the results of those tests.

In the tables the borate activator is $K_2B_4O_7$, the phosphate activator is $K_2HPO_4$ and activator A is nitrilo tris (ethyl phosphoric acid) potassium salt. The water hardness is expressed in ppm of $CaCO_3$.

TABLE III

TYPICAL COMPOSITION OF GLUTARALDEHYDE SOLUTION USED IN TESTS I, II AND III

| | Weight Percent (w/w) | | |
| --- | --- | --- | --- |
| Ingredients | Test I | Test II | Test III |
| Glutaraldehyde | 1.4 | 1.6 | 1.6 |
| Pluronic P103 (surfactant) | 0.1 | 0.1 | 0.1 |
| Activator (Mole Percent) | 0.3 | 0.3 | 0.3 |
| Solution pH | 7.5 | 7.5 | 7.5 |

TABLE IV

TYPICAL COMPOSITION OF GLUTARALDEHYDE SOLUTION USED IN TESTS IV, V AND VI

| | Weight Percent (w/w/) | | |
| --- | --- | --- | --- |
| Ingredients | Test IV | Test V | Test VI |
| Glutaraldehyde | 2 | 2 | 2 |
| Pluronic P103 (surfactant) | 0.2 | 0.2 | 0.2 |
| Polyethylene Glycol | 2 | 6 | 30 |
| Activator (Mole Percent) | 0.3 | 0.3 | 0.3 |
| Solution pH | 7.5 | 7.5 | 7.5 |

TABLE V

GLUTARALDEHYDE SOLUTIONS
Sporicidal Test Results
*Bacillus subtilis* on Silk Sutures, 20° C., 10 Hours Contact
Time - # Failures/# Tested.

| Activator System | Test I | | Test II | | Test III |
|---|---|---|---|---|---|
| Hardness | 100 ppm | 200 ppm | 100 ppm | 200 ppm | 300 ppm |
| Borate | 30/30 | 30/30 | 7/30 | 5/30 | 25/30 |
| Phosphate | 3/30 | 4/30 | 0/30 | 1/30 | 2/30 |
| A | 0/30 | 3/30 | 0/30 | 0/30 | 1/30 |

TABLE VI

GLUTARALDEHYDE/POLYETHYLENE GLYCOL (DIOL)

300 ppm - Hardness

| Activator System | Test IV 2% Diol | Test V 6% Diol | Test VI 30% Diol |
|---|---|---|---|
| Borate | 3/30 | 5/30 | 28/30 |
| Phosphate | 0/30 | 0/30 | 2/30 |
| A | 0/30 | 0/30 | 9/30 |

The data in Tables II and V illustrate that in the presence of hard water the glutaraldehyde solution activated with nitrilo tris (ethyl phosphoric acid) potassium salt (activator A in Table III) had sporicidal activity equal to that of the phosphate activated solution and better activity than that of the borate activated solution.

The data in Tables IV and VI show that similar results in sporicidal activity are obtained when a diol, polyethylene glycol, is added to the solution except that a higher failure rate was obtained with very high (30%) levels of polyethylene glycol.

EXAMPLE III

Glutaraldehyde solutions were tested for sporicidal activity according to the method specified in sections 4.015–4.017 of the AOAC Methods. The organism was tested on silk suture loops and porcelain penicylinder carriers. The solutions contained 3% by weight glutaraldehyde, 1% by weight of the potassium salt of nitrilo tris (ethyl phosphoric acid) and 10% by weight of polyethylene glycol having an average molecular weight of 200. The results are reported as number of failures/number of tests.

| Organism/Carrier | pH of Solution | Results # Failures/ # Tested |
|---|---|---|
| *B. subtilis*/suture | 7.40 | 0/60 |
| *B. subtilis*/penicylinder | 7.40 | 0/60 |
| *C. sporogenes*/suture | 7.66 | 0/60 |
| *C. sporogenes*/penicylinder | 7.66 | 0/60 |

-continued

| Organism/Carrier | pH of Solution | Results # Failures/ # Tested |
|---|---|---|
| *C. sporogenes*/suture | 7.60 | 0/60 |
| *C. sporogenes*/penicylinder | 7.60 | 0/60 |

EXAMPLE IV

A glutaraldehyde solution containing 3% by weight glutaraldehyde and 1% by weight of the potassium salt of nitrilo tris (ethyl phosphoric acid) was tested against various vegetative organisms. The solutions also contained 10% by weight of polyethylene glycol with an average molecular weight of 200. Sixty replicates were run against each test organism. The results are reported below as number of failures/number of tests. The test employed was the AOAC Use Dilution Method as specified in the Official Method of Analysis of the Association of Official Analytic Chemists, Section 4007–4011. The temperature was 20° C. and the exposure time was 10 minutes.

| Organism | pH of Solution | Results # Failures # Tested |
|---|---|---|
| *Pseudomonas aeruginosa* | 7.83 | 0/60 |
| " | 7.68 | 0/60 |
| " | 7.63 | 0/60 |
| *Salmonella choleraesuis* | 7.81 | 0/60 |
| " | 7.66 | 0/60 |
| " | 7.61 | 0/60 |
| *Trichophyton mentagraphytes* | 7.83 | 0/60 |
| " | 7.69 | 0/60 |

I claim:

1. A hard water compatible aqueous sterilizing and disinfecting solution, comprising from 0.05 to 30% by weight of glutaraldehyde and containing a salt of nitrilo tris (ethyl phosphoric acid) as a buffering agent and the ratio of glutaraldehyde to the buffering agent is between 15 to 1 and 1 to 1 and which the salt of nitrilo tris (ethyl phosphoric acid) is the sodium or potassium salt or a mixed sodium and potassium salt.

2. The solution of claim 1 containing from 0.05 to 3.6% glutaraldehyde.

3. The solution of claim 1 containing a diol of the formula $RO(CH_2CH_2O)_nCH_2CH_2OH$ wherein R is H or $CH_3$ and n is an integer from 1 to 22, and the diol is present in a diol to glutaraldehyde ratio of from 2 to 1 to 5 to 1.

4. The solution of claim 1 containing from 10 to 30% glutaraldehyde.

5. The solution of claim 1 in which the glutaraldehyde content is from 2% to 3.6% by weight, and the ratio of glutaraldehyde to the buffering agent is between 5 to 1 and 2 to 1.

* * * * *